(12) United States Patent
Lin et al.

(10) Patent No.: US 9,146,212 B2
(45) Date of Patent: Sep. 29, 2015

(54) THREAD-BASED MICROFLUIDIC GUIDING SYSTEM

(71) Applicant: National Sun Yat-sen University, Kaohsiung (TW)

(72) Inventors: Che-hsin Lin, Kaohsiung (TW); Yi-chi Wei, Kaohsiung (TW); Lung-min Fu, Kaohsiung (TW); Yu-An Yang, Kaohsiung (TW)

(73) Assignee: NATIONAL SUN YAT-SEN UNIVERSITY, Kaohsiung (TW)

( * ) Notice: Subject to any disclaimer, the term of this patent is extended or adjusted under 35 U.S.C. 154(b) by 148 days.

(21) Appl. No.: 13/890,288

(22) Filed: May 9, 2013

(65) Prior Publication Data

US 2013/0299352 A1 Nov. 14, 2013

(30) Foreign Application Priority Data

May 10, 2012 (TW) .............................. 101116744 A

(51) Int. Cl.
*B01L 99/00* (2010.01)
*G01N 35/00* (2006.01)
*G01N 27/447* (2006.01)
*B01L 3/00* (2006.01)

(52) U.S. Cl.
CPC ........ *G01N 27/44791* (2013.01); *B01L 3/5027* (2013.01); *B01L 2300/0645* (2013.01); *B01L 2300/0845* (2013.01); *B01L 2300/0867* (2013.01); *B01L 2300/161* (2013.01); *B01L 2400/0406* (2013.01); *B01L 2400/0421* (2013.01)

(58) Field of Classification Search
CPC ............ G01N 27/44791; B01L 3/5027; B01L 2300/0645; B01L 2300/0845; B01L 2300/0867; B01L 2300/161; B01L 2400/0406; B01L 2400/0421
USPC .................................................. 422/500–508
See application file for complete search history.

(56) References Cited

FOREIGN PATENT DOCUMENTS

TW 1294968 3/2005

OTHER PUBLICATIONS

Yi-Chi Wei; Shin-Yu Su; Lung-Min Fu; Che-Hsin Lin, "Electrophoresis separation and electrochemical detection on a novel line-based microfluidic device," Micro Electro Mechanical Systems (MEMS), 2012 IEEE 25th International Conference on , vol., No., pp. 104, 107, Jan. 29, 2012-Feb. 2, 2012.*

(Continued)

*Primary Examiner* — Lyle Alexander
*Assistant Examiner* — Robert Eom
(74) *Attorney, Agent, or Firm* — Mark M. Friedman

(57) ABSTRACT

A thread-based microfluidic guiding system is provided and includes a substrate, two fiber threads arranged on the substrate in a cross manner. The two fiber threads are used as physical guiding pathways to guide a sample fluid and a buffer fluid, respectively. The two fiber threads have capillary action, so that the sample fluid, the buffer fluid or a mixture fluid thereof can flow along fiber surfaces of the two fiber threads, which can be pre-treated by plasma. The thread-based microfluidic guiding system of the present invention is different from recessed microfluidic channel structures, and can simplify system structure, lower manufacture cost, accelerate detection operation and enhance detection sensitivity.

9 Claims, 6 Drawing Sheets

(56) References Cited

OTHER PUBLICATIONS

Wei, Yi-Chi, et al. "Capillary electrophoresis electrochemical (CE-EC) detection on a novel thread-based microfluidic device with 3D sensing electrodes." Nano/Molecular Medicine and Engineering (NANOMED), 2012 IEEE 6th International Conference on. IEEE, 2012.*

* cited by examiner

THREAD-BASED MICROFLUIDIC GUIDING SYSTEM

FIELD OF THE INVENTION

The present invention relates to a microfluidic guiding system, and especially to a microfluidic guiding system utilizing threads to guide microfluid.

BACKGROUND OF THE INVENTION

A typical microfluidic channel system mainly includes a substrate which is made of glass transparent plastic material and is etched by complicated development etching processes to form grooved microfluidic channels on a surface thereof. Moreover, a basic structure of the microfluidic channel system can be assembled by using another substrate to cover thereon. This type of microfluidic channel system is widely used as a carrier of detections for optics, electrochemistry, and electrochemical electrophoresis analyses.

For example, Taiwan patent No. 1294968 reveals a bio-electrical detection chip, which includes a chip body, a first microchannel, a second microchannel, and a pair of working electrodes. The first microchannel, the second microchannel, and the pair of working electrodes are disposed on the chip body, and the first and second microchannels penetrate through the chip body. The first microchannel is interconnected with the second microchannel. The first microchannel is utilized to guide a sample fluid to flow; the second microchannel is utilized to guide a buffer fluid to flow. The two working electrodes are disposed at both sides the second microchannel, respectively, thereby performing a non-contact electrophoresis analysis.

However, the drawback of the grooved microfluidic channels within the conventional substrates is that surface tension or viscosity of the microfluid influence a capillary action of the microfluid and a rate of the flow along a pipe wall of the microfluidic channel. Furthermore, the greater the surface tension or viscosity, the greater an adhesion force of on the pipe wall is; the longer a flowing duration is.

Thus, it is prone to the problem of poor fluidity. Moreover, if a voltage is applied to the microfluid in the grooved microfluidic channels for carrying on electrochemical analyses such as capillary electrophoresis, a Joule heating effect is easy to generate in the microfluid within the grooved microfluidic channels, thereby affecting a variety of background parameters and accuracy of the experimental results. In addition, if the purpose of the experiment is changed, the shape of the grooved microfluidic channel also needs to be re-fabricated by the complicated development etching processes. Thus, its overall analysis and detection cost is relatively high.

In the channels of the conventional electrophoresis chips, because the substrates are mainly made of glass and polymer organic transparent silicon compound, and because lengths of an injection channel and a separation channel are fixed due to its manufacturing processes, injection volume that is used for separating the sample can not be changed quantitatively. As a result, the analyzed sample which reaches a detection end is a very small amount, resulting in a poor signal to be obtained, or it is not easy to be detected. Therefore, the present system is developed by twining different number of turns of coils, thereby changing the fed amount of the sample in order to achieve a high detection sensitivity.

Therefore, there is a signification need to provide an improved microfluidic guiding system for solving the problem existing in the structure of the conventional grooved microfluidic channels.

SUMMARY OF THE INVENTION

A main objective of the present invention is to provide a thread-based microfluidic guiding system, which disposes two fiber threads on a surface of a substrate to serve as physical guiding pathways. The fiber threads have capillary characteristics which is capable of guiding the microfluid to flow along fiber surface of the fiber threads. The fiber threads can be applied to the analysis and detection of electrochemical electrophoresis and so on, and is capable of effectively radiating heat to the air for reducing the influence to the experimental results due to the Joule heating effect. Meanwhile, the fiber threads have a relatively low cost, and the layout pattern is easy to reset or adjust. Therefore, it is certainly advantageous to simplify the system structure, reduce the production costs and speed up the detection operations. The present invention is capable of detecting not only a single ionic mixed solution but also detecting types of biological samples with good detection results.

Another objective of the present invention is to provide a thread-based microfluidic guiding system, which utilizes the plasma to treat the fiber thread so that the surface thereof becomes more smooth and easy to adsorb the microfluid for flowing along the surface. Thus, the fiber thread can be served as a good guiding pathway, so the hydrophilicity, the hydroscopicity, and the detection sensitivity of the fiber thread can be relatively increased.

Still another objective of the present invention is to provide a thread-based microfluidic guiding system, which can also dispose two bobbins respectively on both ends of the fiber thread for feeding the spare fiber thread and winding the used fiber thread, so the convenience of the fiber thread replacement is relatively improved.

Further another objective of the present invention is to provide a thread-based microfluidic guiding system, which disposes two fiber threads on a surface of a substrate to serve as physical guiding pathways. One of the fiber threads can twine(twist) around the another fiber thread two or more turns, or twine in the fiber thread having different wire diameters. Both of which can be an arrangement with variable intersection. By changing the number of wound turns, the separation amount in the pathways can be changed. Thus, the separation amount in the pathways becomes high, so it is advantageous to improve a signal detection sensitivity of the chip. Because of no need to change a large part of the processes, adjustability thereof is high, and the operation is easy, not time-consuming.

Yet another objective of the present invention is to provide a thread-based microfluidic guiding system, which disposes a plurality of electrodes on a surface of a substrate. The fiber thread can be placed in specially designed electrodes of three-dimensional groove structures. The surface area of actual contact between the electrodes and the fiber thread is able to increase, thereby enhancing the detection sensitivity and accuracy in order to get a better signal quality.

To achieve the foregoing objectives, the present invention provides a thread-based microfluidic guiding system, which includes: a substrate; a first fiber thread disposed on the substrate and sequentially having a sample fluid injection end, a sample fluid transmission section, a first turning portion, a mixture fluid transmission section, and a first waste fluid end, wherein the sample fluid transmission section is turned and coupled to the mixture fluid transmission section through the first turning portion; a second fiber thread disposed on the substrate and sequentially having a buffer fluid injection end, a buffer fluid transmission section, a second turning portion, a waste fluid transmission section, and a second waste fluid end, wherein the buffer fluid transmission section is turned and coupled to the waste fluid transmission section through the second turning portion, and the first turning portion crosses and contacts the second turning portion; and a working electrode disposed on the substrate and contacting the mixture fluid transmission section to form a detection area which is close to the first waste fluid end.

In one embodiment of the present invention, the second fiber thread twines around the first fiber thread two or more turns in the second turning portion; or the first fiber thread twines around the second fiber thread two or more turns in the first turning portion.

In one embodiment of the present invention, the first and second fiber threads have 1 to 100 stands of fibers, respectively.

In one embodiment of the present invention, a diameter of the first fiber thread is between 10 to 200 micrometers; a diameter of the second fiber thread is between 10 to 1500 micrometers.

In one embodiment of the present invention, the first and second fiber threads have a fiber surface treated by a plasma process, respectively.

In one embodiment of the present invention, the fibers of the first and second fiber thread are selected from polyester fibers, nylon fibers, polyimide fibers, and Teflon fibers, respectively.

In one embodiment of the present invention, a first feed bobbin disposed at the sample fluid injection end of the first fiber thread; and a first take-up bobbin disposed at the first waste fluid end thereof.

In one embodiment of the present invention, a second feed bobbin disposed at the buffer fluid injection end of the second fiber thread; and a second take-up bobbin disposed at the second waste fluid end thereof.

In one embodiment of the present invention, the working electrode has a groove with a plurality of interior wall surfaces in contact with the mixture fluid transmission section.

In one embodiment of the present invention, that further includes a counter electrode, which is in contact with the mixture fluid transmission section, close to the working electrode, and located between the working electrode and the first waste fluid end.

In one embodiment of the present invention, the counter electrode has a groove with a plurality of interior wall surfaces in contact with the mixture fluid transmission section.

In one embodiment of the present invention, that further includes a reference electrode, which is in contact with the mixture fluid transmission section, and located between the working electrode and the counter electrode.

In one embodiment of the present invention, the reference electrode has a groove with a plurality of interior wall surfaces in contact with the mixture fluid transmission section.

In one embodiment of the present invention, that further includes a decoupler electrode, which is in contact with the mixture fluid transmission section, close to the working electrode, and located between the first turning portion and working electrode.

In one embodiment of the present invention, the decoupler electrode has a groove with a plurality of interior wall surfaces in contact with the mixture fluid transmission section.

In one embodiment of the present invention, the substrate is made of glass or transparent plastic, wherein the transparent plastic is selected from polymethylmethacrylate, poly(dimethylsiloxane), and polycarbonate.

DETAILED DESCRIPTION OF THE PREFERRED EMBODIMENTS

It is to be understood that both the foregoing general description and the following detailed description of the present invention are exemplary and explanatory and are intended to provide further explanation of the invention as claimed. Moreover, Directional terms mentioned in the present invention, such as "top" and "down", "front", "rear", "left", "right", "inside", "outside", "side" and so on are only directions with respect to the attached drawings. Therefore, the used directional terms are utilized to explain and understand the present invention but not to limit the present invention.

Figure 1:
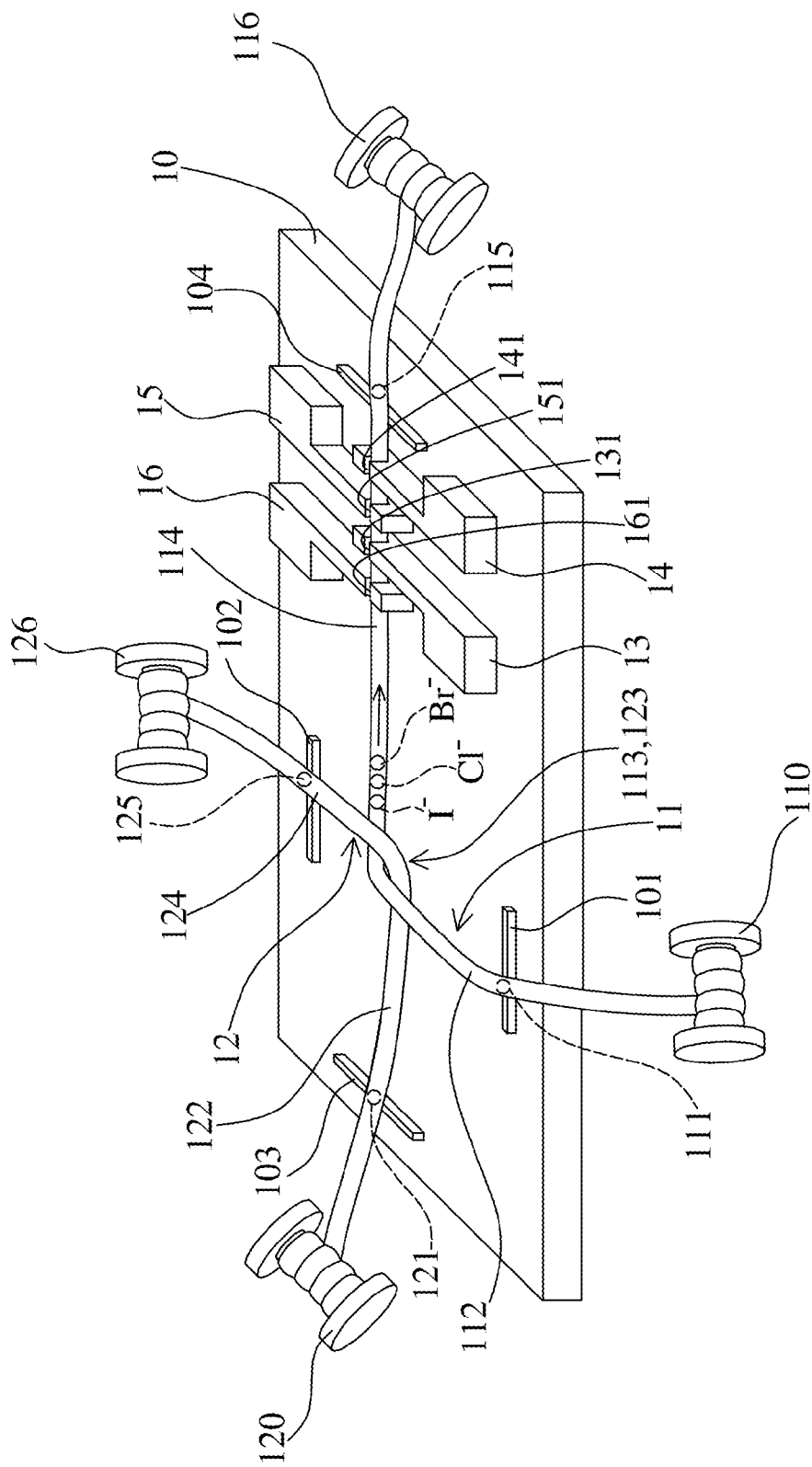
FIG. 1 is a perspective view illustrating a thread-based microfluidic guiding system according to one preferred embodiment of the present invention.

Referring to FIG. 1, the thread-based microfluidic guiding system of the preferred embodiment of the present invention can be applied to the fields of an electrochemical detection analysis, a fluorescent labeled detection analysis, or others using the microfluidic channel to perform biological analysis and detection. In the embodiment, the thread-based microfluidic guiding system of the present invention is used in, for example, an electrochemical electrophoresis analysis detection. The thread-based microfluidic guiding system mainly includes a substrate 10, a first fiber thread 11, a second fiber thread 12, a working electrode 13, a counter electrode 14, a reference electrode 15 and a decoupler electrode 16. The following will explain specific structures, assembly, and working principle in detail with respect to the above-mentioned components of the preferred embodiment according to the present invention by using FIGS. 1 to 4B.

Referring to FIG. 1, the substrate 10 of the preferred embodiment of the present invention is made of glass or transparent plastic. The transparent plastic is selected from polymethylmethacrylate (PMMA), poly(dimethylsiloxane) (PDMS), and polycarbonate (PC), but it is not limited to be implemented in these material. The shape of the substrate 10 may be rectangular, square, circular, or other geometric shapes or special design shapes, and the length and width thereof can be between 10 to 200 mm (millimeters), respectively. In the embodiment, the substrate 10 can be fabricated by, for example, using a rectangular PMMA plate, and the length and width thereof are, for example, 70×30 mm or 60×20 mm.

Moreover, a plurality of electrical contacts 101, 102, 103, and 104, the working electrode 13, the counter electrode 14, the reference electrode 15, and the decoupler electrode 16 are formed in batches or at the same time on a surface (upper surface) of the substrate 10 by using micro hot embossing or other manners. Amongst, in addition to a material of the reference electrode 15 being platinum (Pt), materials of the rest of the electrical contacts 101-104 and the other electrodes 13, 14, 16 are gold (Au), but they are not limited thereto. Thicknesses of said electrical contacts 101-104 and the other electrodes 13, 14, 16 are not limited.

Referring to FIG. 1 again, the first fiber thread 11 of the preferred embodiment of the present invention has preferably 1 to 100 stands of fibers.

For example, the fiber thread can be a single strand of fiber directly, or can be formed by using 2, 5, 10, 20, 25, 50, 75, 80 or 100 strands of fibers to crossly weave. A diameter of the first fiber thread 11 may be between 10 to 200 micrometers, for example 10, 50 or 200 microns, but it is not limited thereto. Moreover, the fibers of the first fiber thread may be selected from polyester fibers, nylon fibers, polyimide fibers, and Teflon fibers. Preferably, the polyester fiber is selected, and its glass transition temperature is greater than 190° C.; therefore, it can relatively meet a demand of material stability under a high-temperature operation of the electrochemical electrophoresis.

Figure 2A:
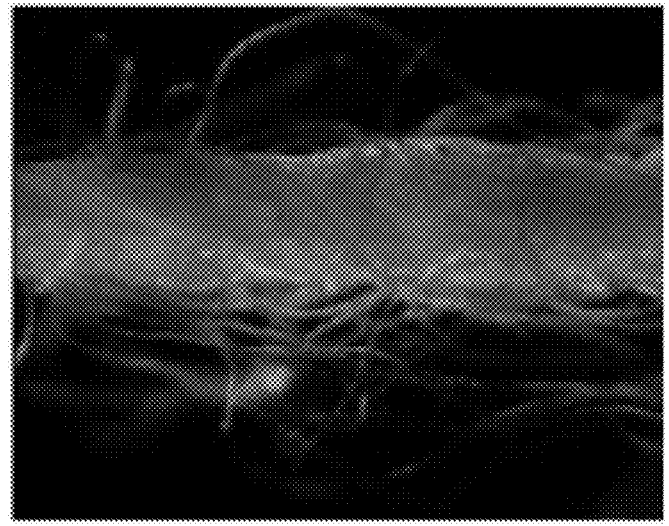
FIG. 2A and FIG. 2B are pictures illustrating surface morphologies of fiber threads (a control group and an experimental group, and a wire diameter is 200 micrometers) treated or untreated by a plasma process.
Figure 2B:
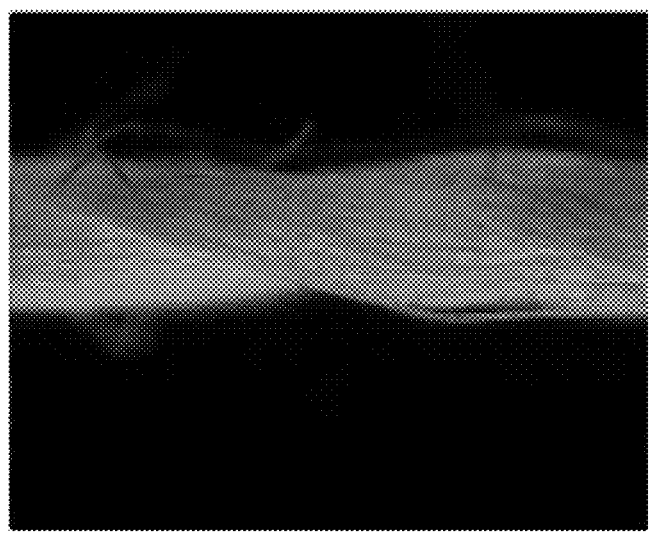

Referring to FIG. 2A and FIG. 2B, the figures disclose surface morphologies of the fiber threads (a control group and an experimental group, and the wire diameter is 200 micrometers) treated or untreated by a plasma process, respectively.

The present invention can employ, for example, an oxygen plasma system (110 W) to perform the plasma treatment (10 mins, 50-55° C.) onto the fiber surface of the first fiber thread 11. It can be seen from the comparison between FIG. 2A and FIG. 2B that after the fiber surface of the first fiber thread 11 is treated by the plasma process (FIG. 2B), the surface thereof becomes more smooth and easy to adsorb the microfluid for flowing along the surface. Thus, the first fiber thread 11 can be served as a good guiding pathway, so hydrophilicity, hydroscopicity, and detection sensitivity of the first fiber thread 11 can be relatively increased. Significantly, in order to ensure that the hydrophilic and hygroscopic thereof do not decay over time, the fiber surface of the first fiber thread 11 is treated by the plasma process preferably before performing the electrochemical electrophoresis.

Referring to FIG. 1 again, the stands of fibers and the material of the second fiber thread 12 of the preferred embodiment of the present invention are substantially the same as these of the above-mentioned first fiber thread 11. Furthermore, the second fiber thread 12 preferably also has the fiber surface treated by treated by the plasma process. The diameter of the second fiber thread 12 may be between 10 to 1500 micrometers, for example 10, 50 200, 500, 100 or 1500 microns.

Referring to FIG. 1 again, as to the assembly relation, the first fiber thread 11 and second fiber thread 12 are mounted on the substrate 10 by means of 90 degrees intersection and bending, or the intersection can be formed in other acute or obtuse angles. The first fiber thread 11 sequentially has a first feed bobbin (bobbin/roller) 110, a sample fluid injection end 111, a sample fluid transmission section 112, a first turning portion 113, a mixture fluid transmission section 114, a first waste fluid end 115 and a first take-up bobbin 116. Meanwhile, the second fiber thread 12 sequentially has a second feed bobbin 120, a buffer fluid injection end 121, a buffer fluid transmission section 122, a second turning portion 123, a waste fluid transmission section 124, a second waste fluid end 125 and a second take-up bobbin 126.

More specifically, several turns of the unused first fiber thread 11 are wound on the first feed bobbin 110 to provide an automatic thread feeding function with the use of a miniature electric motor. The first fiber thread 11 of the first feed bobbin 110 directly extends to the substrate 10 from a long side (front side) of the substrate 10. The electrical contact 101 is disposed close an edge of the long side on the substrate 10. The position that the first fiber thread 11 contacts the electrical contact 101 is defined as the sample fluid injection end 111. A sample fluid (not shown) with unidentified sample can be titrated onto the sample fluid injection end 111. The first fiber thread 11 extends a predetermined distance along a transverse direction of the substrate 10 from the sample fluid injection end 111, and reaches the first turning portion 113 for intersecting and contacting the second fiber thread 12. A section between the sample fluid injection end 111 and the first turning portion 113 of the first fiber thread 11 is defined as the sample fluid transmission section 112.

Subsequently, after the 90 degrees bending forms at the first turning portion 113, the first fiber thread 11 instead extends a predetermined distance along a longitudinal direction of the substrate 10, and reaches the first waste fluid end 115 for contacting the electrical contacts 104 on the substrate 10. A section between the first turning portion 113 and the first waste fluid end 115 of the first fiber thread 11 is defined as the mixture fluid transmission section 114. Finally, the first fiber thread 11 extends from the first waste fluid end 115 and away from a short side (right side) of the substrate 10, and ultimately is received in the first take-up bobbin 116. The first take-up bobbin 116 provides an automatic thread receiving function with the use of a miniature electric motor.

On the other hand, similarly, several turns of the unused second fiber thread 12 are wound on the second feed bobbin 120 to provide an automatic thread feeding function with the use of a miniature electric motor. The second fiber thread 12 of the second feed bobbin 120 directly extends to the substrate 10 from the other short side (left side) of the substrate 10. The electrical contact 103 is disposed close to an edge of the short side on the substrate 10. The position that the second fiber thread 12 contacts the electrical contact 103 is defined as the buffer fluid injection end 121. A buffer fluid (not shown) can be titrated onto the buffer fluid injection end 121. The second fiber thread 12 extends a predetermined distance along the longitudinal direction of the substrate 10 from the buffer fluid injection end 121, and reaches the second turning portion 123 for intersecting and contacting the first fiber thread 11. A section between the buffer fluid injection end 121 and the second turning portion 123 of the second fiber thread 12 is defined as the buffer fluid transmission section 122.

Subsequently, after the 90 degrees bending forms at the second turning portion 123, the second fiber thread 12 instead extends a predetermined distance along the transverse direction of the substrate 10, and reaches the second waste fluid end 125 for contacting the electrical contacts 102 on the substrate 10. A section between the second turning portion 123 and the second waste fluid end 125 of the second fiber thread 12 is defined as the waste fluid transmission section 124. Finally, the second fiber thread 12 extends from the second waste fluid end 125 and away from the other long side (rear side) of the substrate 10, and ultimately is received in the second take-up bobbin 126. The second take-up bobbin 126 provides an automatic thread receiving function with the use of a miniature electric motor.

Referring to FIG. 1 again, the decoupler electrode 16, working electrode 13, reference electrode 15 and counter electrode 14 of preferred embodiment of the present invention are sequentially arranged on a region close to the first waste fluid end 115 on the substrate 10 from left to right. Each of these contacts the mixture fluid transmission section 114, and a distance between any two adjacent electrodes is controlled at approximately 10 mm. A electrode width of each of the electrodes 13-16 in contact with the mixture fluid transmission section 114 is approximately 500 μm (microns), but it is not limited thereto. The working electrode 13 is also known as an operation electrode. The counter electrode 14 is also known as an opposite electrode, which is located between the working electrode 13 and the first waste fluid end 115. The reference electrode 15 is located between the working electrode 13 and the counter electrode 14; the decoupler electrode 16 is located between the first turning portion 113 and the working electrode 13.

As to functions of the electrodes, the electrical contacts 101, 102, 103, and 104 are contacts the sample fluid injection end 111 of the first fiber thread 11, the second waste fluid end 125 of the second fiber thread 12, the buffer fluid injection end 121 of the second fiber thread 12, and the first waste fluid end 115 of the first fiber thread 11, respectively. The electrical contacts 101 and 102 can be coupled to a negative polarity and a positive polarity (or contrary setting) of a power supply, respectively; meanwhile, the electrical contacts 103 and 104 can be coupled to the negative polarity and the positive polarity (or contrary setting) of the power supply, respectively. Accordingly, a separation electric field (e.g., +0.78 V, 300 to 400 V/cm) can be formed between the sample fluid injection end 111 and the second waste fluid end 125, and another separation electric field (e.g., +0.78 V, 300 to 400 V/cm) can be formed between the buffer fluid injection end 121 and the first waste fluid end 115.

Moreover, the electrode 13-16 can be electrically coupled to a current measurement unit (not shown), respectively. A portion of the working electrode 13 herein in contact with the mixture fluid transmission section 114 forms a detection area (not shown). The working electrode 13 can detect a current value caused by ions (e.g. $Cl^-$, $Br^-$, $I^-$, etc.) passing through the detection area along the mixture fluid transmission section 114. The counter electrode 14 is utilized to apply a voltage value (for example, −1.0 V~+1.0 V) to a mixture fluid on the mixture fluid transmission section 114. The material (Pt) of the reference electrode 15 has a great deal of resistance, so it only allows a very small amount of current to pass through that for holding a potential. Thus, it is advantageous to precisely obtain and control the applied voltage value of the counter electrode 14, so as to stably control the potential which is applied to the working electrode 13, and thus to ensure that the accuracy of the subsequent current/voltage value analyses. The decoupler electrode 16 is utilized to form a conductive region prior to the above-mentioned detection area, so that the voltage of the separation electric field to decrease rapidly while the voltage reaches this detection area, in order to avoid reducing degree of the ion separation.

When the separated electrochemical substances (e.g. the ions) flow through the electrode surface of the working electrode 13 along the mixture fluid transmission section 114, due to a potential difference existing between the mixture fluid and the working electrode 13, the electro-active substances (ions) in the mixture fluid will be oxidized or reduced, and a weak current is formed between the mixture fluid and the electrodes. The current obeys Faraday's law, that is, the current being proportional to the concentration of the analyzed substances. The weak current is detected by an amplifier, and its variation over time can be recorded for obtaining a current variation graph of the electrophoresis.

Figure 3A:
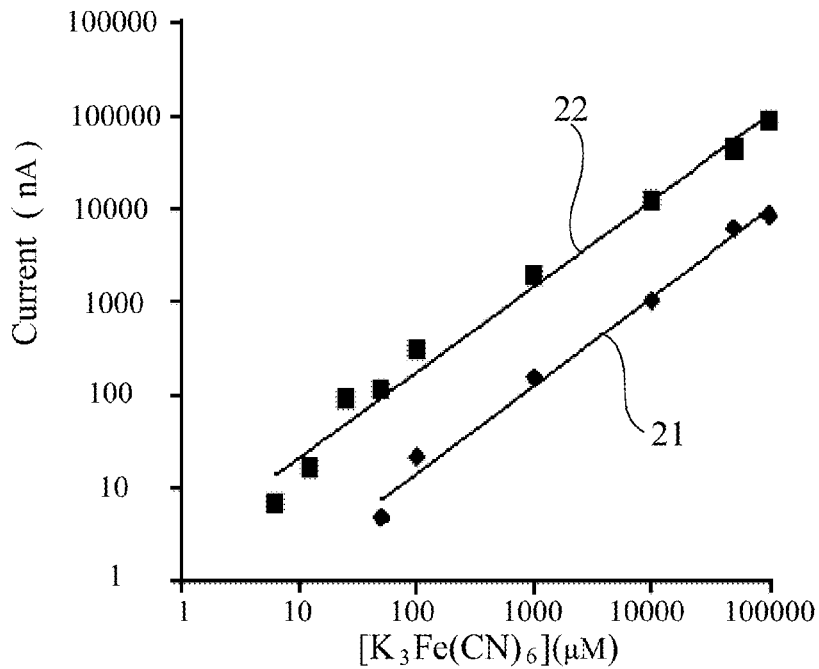
FIG. 3A is a sample concentration-current graph with respect to a detected mixture fluid containing potassium ferricyanide by using the fiber threads (the control group and experimental group), which are treated or untreated by the plasma process.
Figure 3B:
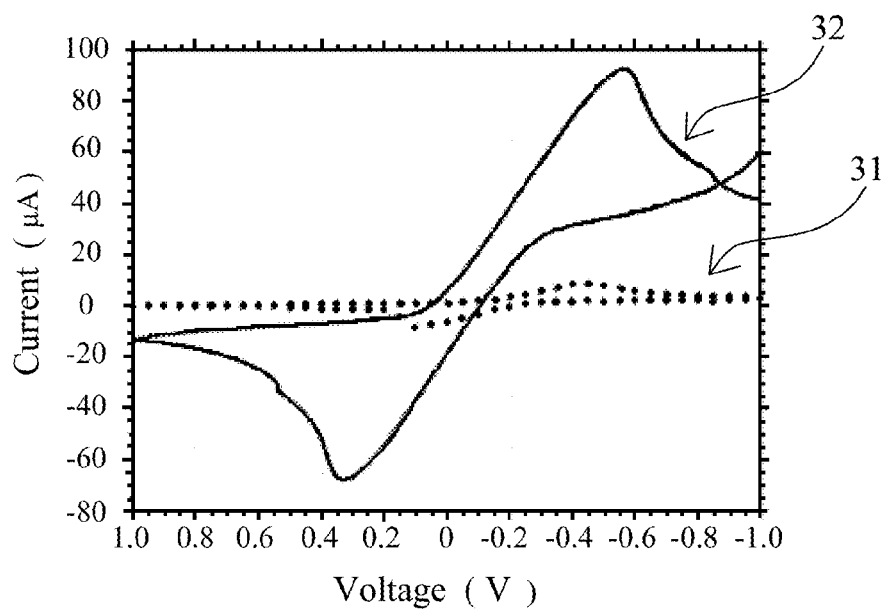
FIG. 3B a separation voltage-current graph with respect to the detected mixture fluid containing potassium ferricyanide by using the fiber threads (the control group and experimental group), which are treated or untreated by the plasma process.

Referring to FIG. 3A and FIG. 3B, FIG. 3A reveals a sample concentration-current graph with respect to the detected mixture fluid containing potassium ferricyanide ($K_3Fe(CN)_6$) by using the fiber threads (control group and experimental group), which are treated or untreated by the plasma process; FIG. 3B reveals a voltage-current graph with respect to the voltages of the separation electric field and the currents of the control group and the experimental group.

When the detection is performed by using the thread-based microfluidic guiding system of FIG. 1, a sample fluid containing the potassium ferricyanide (concentration: 100 mM) is titrated onto the sample fluid injection end 111 of the first fiber thread 11 first, and a MES buffer fluid (concentration: 0.1 mM) is titrated onto the buffer fluid injection end 121 of the second fiber thread 12. Subsequently, the electrical contacts 103, 104 are coupled to a power supply, respectively, so that a separation electric field (e.g., +0.78 V, 300 to 400 V/cm) can be formed between the sample fluid injection end 111 and the second waste fluid end 125, and another separation electric field (e.g., +0.78 V, 300 to 400 V/cm) can be formed between the buffer fluid injection end 121 and the first waste fluid end 115.

Under the driving of the actions of the capillary and the separation electric field, The potassium ferricyanide sample fluid flows to the first turning portion 113 along the surface of the sample fluid transmission section 112; the buffer fluid flows to the second turning portion 123 along the buffer fluid transmission section 122. In the intersection region of the first turning portion 113 in contact with the second turning portion 123, the potassium ferricyanide sample fluid and the buffer fluid are mixed together, and the obtained mixture fluid which contains potassium ferricyanide flows along the mixture fluid transmission section 114 and toward the first waste fluid end 115. In addition, another generated waste fluid flows along the waste fluid transmission section 124 and toward the second waste fluid end 125.

Therefore, the working electrode 13 can detect the current value caused by ions ($CN^-$) passing through the detection area along the mixture fluid transmission section 114. By using the same method to carry on the current value detections for the potassium ferricyanide sample fluid with various concentrations (10 μM to 100 mM), the results can be obtained as shown in FIG. 3A. Two current trend lines 21 and 22 herein represent the fiber thread (the control group) without the plasma treatment and the fiber thread (the experimental group of the present invention) with the plasma treatment, respectively. By changing the voltage value (+1.0~−1.0V) of the separation electric field to carry on the current value detections under the same concentration, the results can be obtained as shown in FIG. 3B. A redox current curve 31 herein indicates the fiber thread (the control group) without the plasma treatment, and another redox current curve 32 indicates the fiber thread (the experimental group of the present invention) with the plasma treatment. It can be seen form FIGS. 3A and 3B that the fiber thread (the experimental group of the present invention) with the plasma treatment is certainly conducive to obtain a stronger current signal.

Figure 4A:
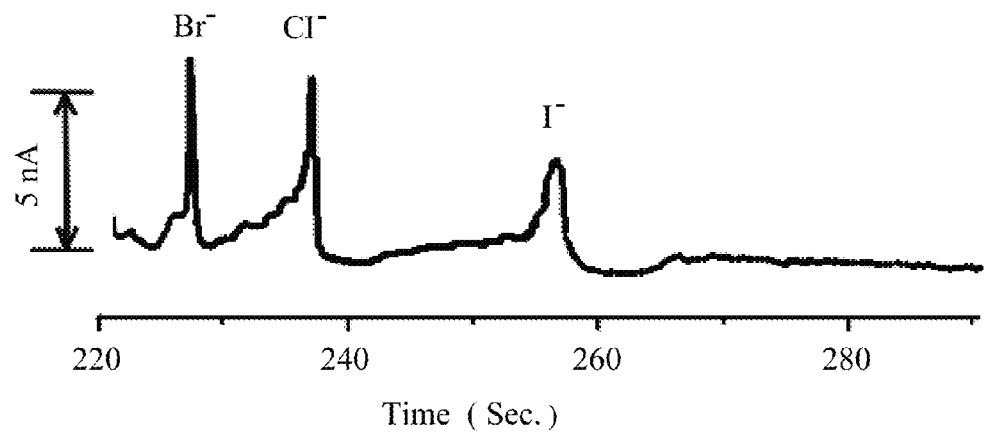
FIG. 4A and FIG. 4B are time-current graphs with respect to the detected mixture fluid containing chlorine, bromine, iodine ions by using the fiber threads (the control group and experimental group), which are treated or untreated by the plasma process.
Figure 4B:
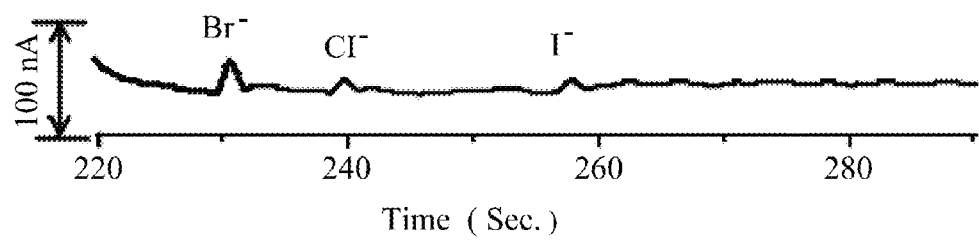

In addition, referring to FIG. 4A and FIG. 4B, the figures disclose time-current graphs with respect to the detected mixture fluid containing chlorine, bromine, iodine ions ($Cl^-$, $Br^-$, $I^-$) by using the fiber threads (the control group and experimental group), which are treated or untreated by the plasma process, respectively. Here, by using similar steps as described in FIG. 3A, the sample fluid is only altered as a sample Fluid containing potassium chloride (0.3 mm KCl), sodium bromide (0.3 mM NaBr) and sodium iodide (0.3 mM NaI), thereby comparing the strengths of the current values of the detected ions ($Cl^-$, $Br^-$, $I^-$) of the control group and the experimental group at different time points. It can be seen from the results that although the control group of FIG. 4A has an excellent detection capability of the ion separation, the strengths of the current signal are insufficient, and noise ratios (3, 6, 2.4) of the ions (Cl$^-$, Br$^-$, I$^-$) are still low. The experimental group of FIG. 4B has not only an excellent detection capability of the ion separation, and the strengths of the current signal are sufficient, and the noise ratios (29.5, 32, 17.5) of the ions (Cr$^-$, Br$^-$, I$^-$) are significantly improved.

As mentioned above, in comparison with the drawbacks of the mobility, the Joule heat effect and the complicated manufacture procedure existing in the conventional grooved microfluidic channel structure, the present invention of FIG. 1 disposes two fiber threads on a surface of a substrate to serve as physical guiding pathways. The fiber thread has capillary characteristics which is capable of guiding the microfluid to flow along fiber surface of the fiber threads. The fiber threads can be applied to the analysis and detection of electrochemical electrophoresis and so on, and is capable of effectively radiating heat to the air for reducing the influence to the experimental results due to the Joule heating effect. Meanwhile, the fiber threads have a relatively low cost, and the layout pattern is easy to reset or adjust. Therefore, it is certainly advantageous to simplify the system structure, reduce the production costs and speed up the detection operations.

Moreover, the present invention utilizes the plasma to treat the fiber thread so that the surface thereof becomes more smooth and easy to adsorb the microfluid for flowing along the surface. Thus, the fiber thread can be served as a good guiding pathway, so the hydrophilicity, the hydroscopicity, and the detection sensitivity of the fiber thread can be relatively increased. In addition, the present invention can also dispose two bobbins on both ends of the fiber thread for feeding the spare fiber thread and winding the used fiber thread, respectively, so the convenience of the fiber thread replacement is relatively improved.

Figure 5:
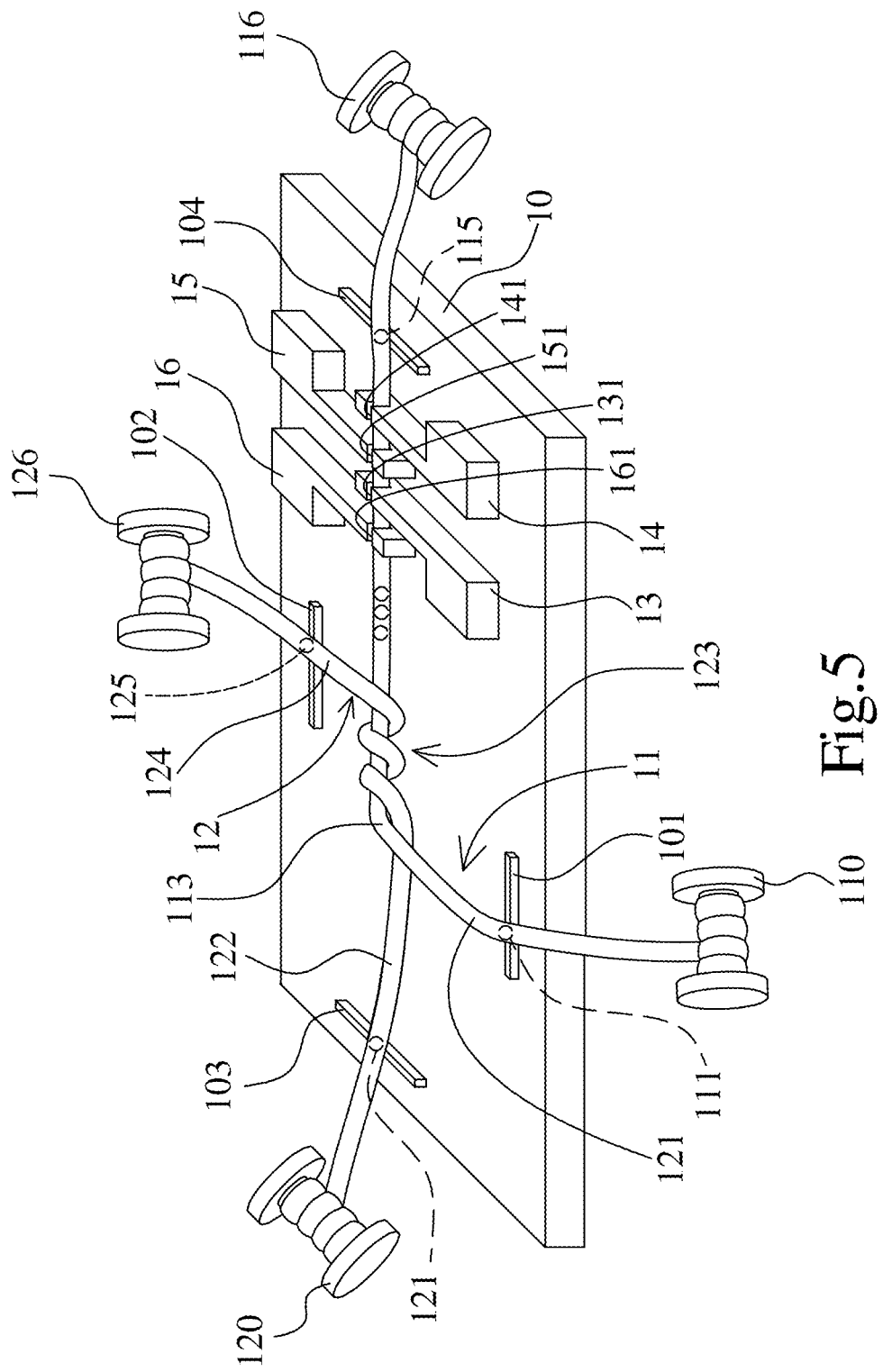
FIG. 5 and FIG. 6 are perspective views illustrating the thread-based microfluidic guiding system according to another two embodiment of the present invention.
Figure 6:
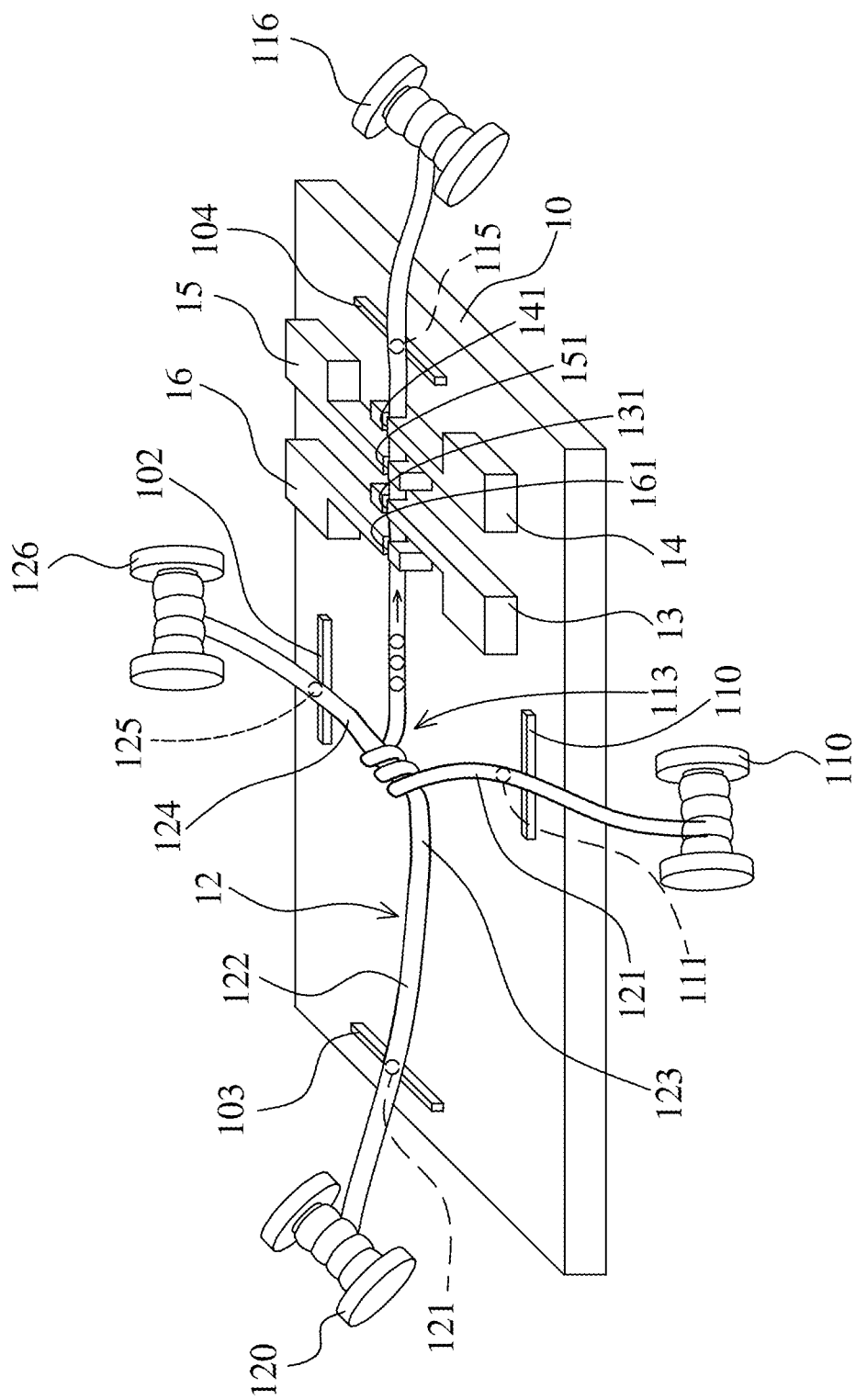

Referring to FIG. 5 and FIG. 6, the figures reveal perspective views of the thread-based microfluidic guiding system according to another two embodiments of the present invention. The two embodiments are substantially the same as the preferred embodiment of FIG. 1. However, in the embodiment of FIG. 5, the second fiber thread 12 twines around the first fiber thread 11 two or more turns, such as 2, 3, 4, 5 or more, in the second turning portion 123, or twines in the fiber thread having different wire diameters. In the embodiment of FIG. 6, the first fiber thread 11 twines around the second fiber thread 12 two or more turns, such as 2, 3, 4, 5 or more, in the first turning portion 113. Meanwhile, in the two embodiments of FIG. 5 and FIG. 6, the working electrode 13, counter electrode 14, reference electrode 15 and decoupler electrode 16 become three-dimensional electrodes with thickness increase, and grooves 131, 141, 151, and 161 are formed thereon, respectively. Each of the grooves 131, 141, 151, and 161 has a plurality of three-dimensional interior wall surfaces (i.e. three interior wall surfaces) utilized to contact the mixture fluid transmission section 114.

Accordingly, through a simple improvement, the variable fiber thread winding design and the three-dimensional groove electrodes are added to the system. First, the second fiber thread 12 (or the first fiber thread 11) are wound around the second turning portion 123 (or the first turning portion 113) with different number of turns in a clockwise or counterclockwise direction. Sample fluid, such as dopamine (0.5 mM) and vitamin C (0.5 mM Ascorbic acid), is completely filled in the sample fluid transmission section 112, and transferred to the mixture fluid transmission section 114 after sufficiently mixed with a buffer fluid from the buffer fluid transmission section 122 at the second turning portion 123 (or the first turning portion 113). Then a separation electric field is applied, and the detection is performed through the grooves 131, 141, 151, and 161 of the working electrode 13, the counter electrode 14, the reference electrode 15 and the decoupler electrode 16. Due to the increase in the number of the wound turns for increasing the sample that reaches the detection ends of the three-dimensional groove electrodes, the concentration of ions in the sample will also become high. S/N ratios of the dopamine and the vitamin C with respect to the different wound turns are: (6.32, 6.06) for 1 wound turn, (12.08, 11.49) for 2 wound turns, (20.74, 19.98) for 3 wound turns, (22.37, 21.48) for 4 wound turns, and (23.04, 22.26) for 5 wound turns. It can be seen from this that the better S/N ratios (20.74, 19.98) can be achieved for 3 wound turns, and then the results thereof for 4 and 5 wound turns are flatten out.

Meanwhile, the surface area of the grooves 131, 141, 151, and 161 of the working electrode 13, the counter electrode 14, the reference electrode 15 and the decoupler electrode 16 in contact with the mixture fluid transmission section 114 increases, thereby making the resistance smaller, the current value larger, and the redox reaction more obvious. Thus, it is advantageous to the detection of the signal, so as to substantially increase the detection sensitivity.

The above-mentioned thread-based microfluidic guiding system can also be applied to the detection for biological samples. For example, a biological sample detection can be based on urea (10 mM) and urease (20 mg/ml). Firstly, the first the first fiber thread 11 is immersed in the urease for the fibers of the thread completely adsorbing urease. Then the first fiber thread 11 and the second fiber thread 12 are variably wound together (as shown in FIG. 5 or FIG. 6), and then the sample urea is added in the sample fluid injection end 111; the buffer fluid is dropped into the buffer fluid injection end 121. Then the separation electric field is applied to the both ends for the sample fluid injection end 111 being at 200V/cm and the buffer fluid injection end 121 being at 300V/cm, respectively. The urea $CO(NH_2)_2$ and the urease in the pathways are mixed to generate $NH4^+$, $HCO_3^-$, and $OH^-$. The above-mentioned generated ions are driven to move to the detection area due to the separation electric field, and detected by the three-dimensional groove electrodes, so that the change of the current signal can be measured. Thus, it can be used to detect urine to know whether a problem of kidney detoxification function is discovered. When the concentration of the urea is too high, the person may be suffering from uremia dialysis, or urinary tract obstruction, gastrointestinal bleeding and so on.

While the preferred embodiments of the present invention have been illustrated and described in detail, various modifications and alterations can be made by persons skilled in this art. The embodiment of the present invention is therefore described in an illustrative but not restrictive sense.

What is claimed is:

1. A thread-based microfluidic guiding system, comprising:
   a substrate;
   a first fiber thread disposed on the substrate and sequentially having a sample fluid injection end, a sample fluid transmission section, a first turning portion, a mixture fluid transmission section, and a first waste fluid end, wherein the sample fluid transmission section is turned and coupled to the mixture fluid transmission section through the first turning portion;
   a second fiber thread disposed on the substrate and sequentially having a buffer fluid injection end, a buffer fluid transmission section, a second turning portion, a waste fluid transmission section, and a second waste fluid end, wherein the buffer fluid transmission section is turned and coupled to the waste fluid transmission section through the second turning portion, and the first turning portion crosses and contacts the second turning portion;

a working electrode disposed on the substrate and contacting the mixture fluid transmission section to form a detection area which is close to the first waste fluid end;

a counter electrode which is disposed on the substrate and in contact with the mixture fluid transmission section, close to the working electrode, and located between the working electrode and the first waste fluid end;

a reference electrode which is disposed on the substrate and in contact with the mixture fluid transmission section, and located between the working electrode and the counter electrode; and a decoupler electrode which is disposed on the substrate and in contact with the mixture fluid transmission section, close to the working electrode, and located between the first turning portion and working electrode;

wherein each of the working electrode, the counter electrode, the reference electrode and the decoupler electrode has a flat top surface parallel to a top surface of the substrate, and a groove configured as a depression in the flat top surface and having a plurality of interior wall surfaces for contacting with the mixture fluid transmission section.

2. The thread-based microfluidic guiding system of claim 1, wherein the second fiber thread twines around the first fiber thread two or more turns in the second turning portion.

3. The thread-based microfluidic guiding system of claim 1, wherein the first fiber thread twines around the second fiber thread two or more turns in the first turning portion.

4. The thread-based micro-fluidic guiding system of claim 1, wherein the first and second fiber threads have 1 to 100 strands of fibers, respectively.

5. The thread-based microfluidic guiding system of claim 1, wherein a diameter of the first fiber thread is between 10 to 200 micrometers; a diameter of the second fiber thread is between 10 to 1500 micrometers.

6. The thread-based microfluidic guiding system of claim 1, wherein the first and second fiber threads have a fiber surface treated by a plasma process, respectively.

7. The thread-based microfluidic guiding system of claim 1, wherein the fibers of the first and second fiber thread are selected from polyester fibers, nylon fibers, polyimide fibers, and TEFLON® fibers, respectively.

8. The thread-based microfluidic guiding system of claim 1, further comprising: a first feed bobbin disposed at the sample fluid injection end of the first fiber thread; and a first take-up bobbin disposed at the first waste fluid end thereof.

9. The thread-based microfluidic guiding system of claim 1, further comprising: a second feed bobbin disposed at the buffer fluid injection end of the second fiber thread; and a second take-up bobbin disposed at the second waste fluid end thereof.

* * * * *